United States Patent [19]

Prather et al.

[11] 4,294,987

[45] Oct. 13, 1981

[54] PROCESS FOR PREPARING METHYLENE DIANILINES

[75] Inventors: Richard A. Prather; Nirad N. Shah, both of Houston, Tex.

[73] Assignee: The Upjohn Company, Kalamazoo, Mich.

[21] Appl. No.: 108,522

[22] Filed: Dec. 31, 1979

[51] Int. Cl.³ .......................................... C07C 85/145
[52] U.S. Cl. ............................ 564/331; 260/453 PH; 260/453 AM; 564/332; 564/333; 564/334
[58] Field of Search ................... 260/570 D; 564/331, 564/332, 333

[56] References Cited

U.S. PATENT DOCUMENTS

| | | | |
|---|---|---|---|
| 3,676,497 | 7/1972 | Recchia et al. | 260/570 |
| 3,857,890 | 12/1974 | Recchia et al. | 260/570 |
| 3,971,829 | 7/1976 | Marquis | 260/570 |
| 4,061,678 | 12/1977 | Knofel et al. | 260/570 |
| 4,071,558 | 1/1978 | Bentley | 260/570 |

*Primary Examiner*—Robert V. Hines
*Attorney, Agent, or Firm*—Denis A. Firth; John Kekich

[57] ABSTRACT

An improvement is described in the process of preparing polymethylene polyphenyl polyamines by condensing aniline and formaldehyde in the presence of an acid catalyst in the initial condensation. The improvement enables the amount of acid which has to be neutralized at the end of the reaction to be substantially reduced or eliminated entirely. This is accomplished without sacrifice of the high level of 4,4'-isomer of di(aminophenyl)methane normally present in the diamine content of the polyamines when a mineral acid catalyst is employed in the condensation. The improvement comprises conducting the initial condensation of aniline and formaldehyde in the presence of a strong acid at a level normally employed to obtain high 4,4'-isomer content in the diamine component of the polyamine product, subjecting the reaction mixture, at the stage at which benzylamine formation is substantially complete, to solvent extraction after adjusting the aniline and water content of the reaction mixture to specified levels, recovering the mixture of benzylamine and excess aniline from the solvent extract and subjecting this mixture (optionally after removal of aniline) to rearrangement to the desired polyamine product in the presence of a catalyst which can be a strong acid (at a level substantially below that used in the initial condensation), or a solid catalyst (diatomaceous earth, clay, zeolite). The aqueous layer remaining after the solvent extraction contains aniline hydrochloride and a minor amount of benzylamine hydrochloride and is recovered and used as part of the reactants employed in a subsequent condensation.

8 Claims, 1 Drawing Figure

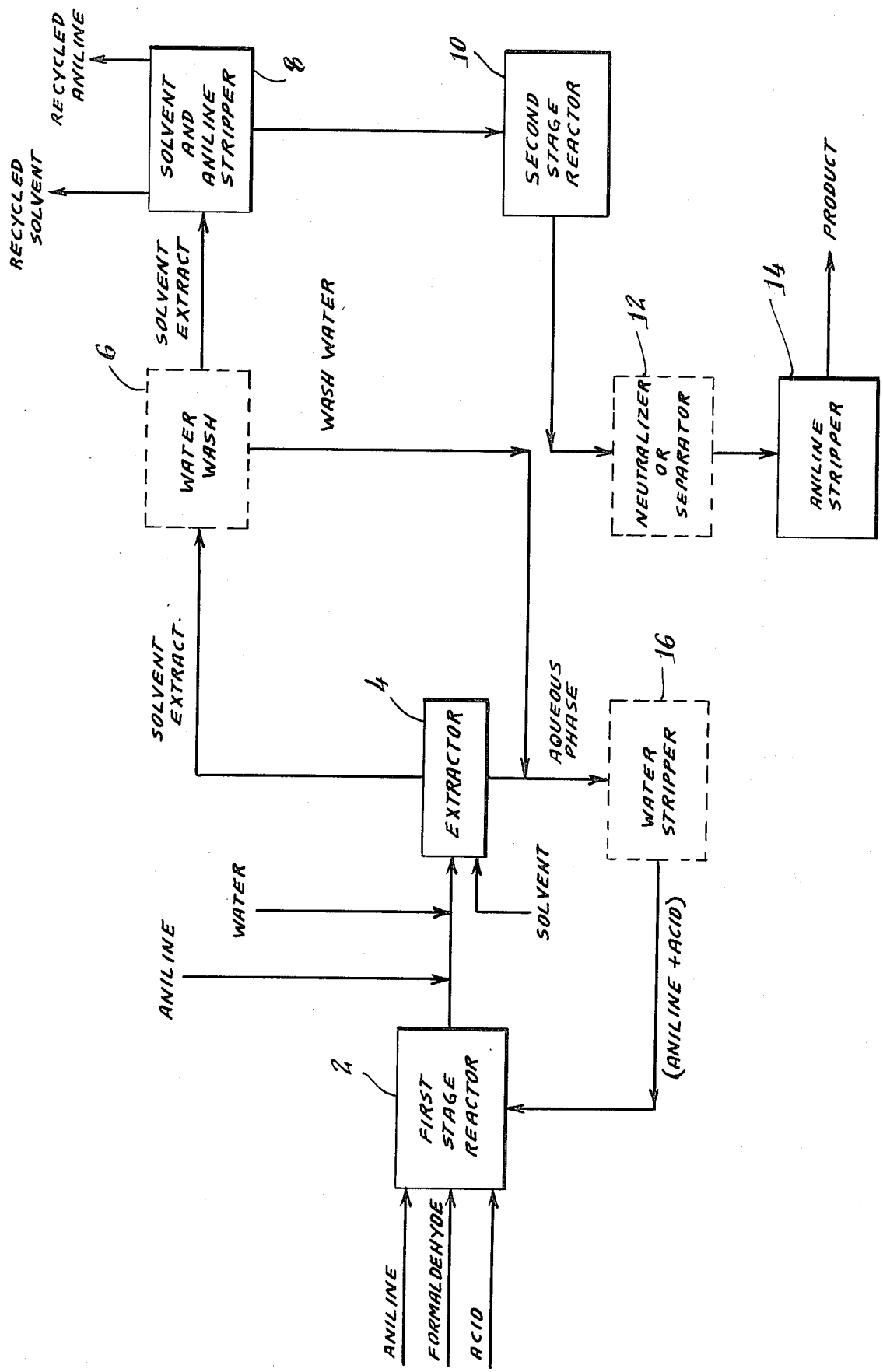

PROCESS FOR PREPARING METHYLENE DIANILINES

BACKGROUND OF THE INVENTION

1. Field of the Invention

This invention relates to the preparation of polyamines and is more particularly concerned with an improved process for the condensation of aniline and formaldehyde to yield polyamine mixtures.

2. Description of the Prior Art

The preparation of the mixtures of methylene-bridged polyphenyl polyamines (hereafter polymethylene polyphenyl polyamines) containing di(aminophenyl)methanes by condensation of aniline and formaldehyde under aqueous conditions in the presence of strong acids, particularly hydrochloric acids, has been widely described. Illustrative of such processes are those shown in U.S. Pat. Nos. 2,638,730; 2,950,263; 3,260,751; 3,277,173; 3,297,759 and 3,476,806. Such processes, in one form or another, are widely used commercially to prepare the polyamines in question, which polyamines are employed as intermediates in the preparation of the corresponding isocyanates, i.e. diisocyanatodiphenylmethane and mixtures of polymethylene polyphenyl polyisocyanates. The isocyanates are employed in the preparation of a variety of polyurethanes, polyisocyanurates and other polymers (both cellular and non-cellular) which can be derived from polyisocyanates.

For many purposes it is desirable that the diamine content of the above polyamines, and the diisocyanate content of the polyisocyanates derived therefrom, contain a high proportion of 4,4'-isomer and this has been achieved largely by employing proportions of strong acid in the condensation of the aniline and formaldehyde with the aniline present in an amount of at least 2 mole per mole of formaldehyde. If the amount of acid is reduced significantly below the above minimum, the proportion of 4,4'-isomer in the diamine component of the reaction product is reduced.

There are a number of reasons why it is undesirable to use these high concentrations of strong acid in the condensation. Thus, the presence of the strong acid, particularly in the later stages of the condensation which are conducted at elevated temperature, represents a serious corrosion problem involving constant repair and maintenance requirements which contribute significantly to the overhead cost of operation of the manufacturing plants in which such processes are utilized. Secondly, the acid in question has to be neutralized, usually by means of aqueous sodium hydroxide, at the end of the reaction and disposal of the resulting neutral salt solution represents a severe problem because of the vast volumes of such material which are generated.

Processes have been described which eliminate the use of the strong acid catalysts and the necessity to neutralize the reaction products and substitute solid catalysts such as clay, zeolites and diatomaceous earth; see, for example, U.S. Pat. Nos. 3,362,979; 4,039,580; and 4,039,581. However, these processes give rise to products in which the 4,4'-isomer content of the diamine is substantially reduced in favor of the 2,4'-isomer and, in some cases, the 2,2'-isomer.

Attempts have been made to solve the problem of the necessity of neutralizing the strong acid catalysts at the end of the reaction by subjecting the final reaction mixture to solvent extraction to isolate the desired diamines and recycling the aqueous solution, containing the acid in the form of amine salt, to reaction mixture employed in a subsequent condensation. The strong acid is thereby recycled without the necessity to neutralize and convert to a salt requiring disposal. Typical of such processes are U.S. Pat. Nos. 3,996,283; 4,025,557; 4,087,459; 4,094,907; and 4,130,588. However, such processes only partially solve the overall problem since the strong acid is still present during the stage of the condensation which is carried out at elevated temperature.

We have now devised a process which offers a solution to both problems since it permits the total elimination or, at least, a significant reduction in the amount of strong acid present in the portion of the condensation carried out above room temperature. It follows that our process also results in elimination of, or significant reduction in, the acid which has to be neutralized at the end of the reaction. Our process, which will be described in detail below, involves extracting the product of condensation, at an intermediate stage prior to the final reaction at elevated temperature, to separate the intermediate condensation product from the aqueous acid reaction product containing the strong acid. The latter aqueous layer is reused in a subsequent aniline-formaldehyde condensation. The solvent extract is then subjected to the final stage of the reaction in the presence of a catalyst which can be a solid catalyst or a strong acid catalyst present in an amount which is significantly less than would be present if the acid used in the initial condensation had been retained for the second stage.

The process which is described herein is therefore differentiated from that described in British Specification No. 1,536,008. In the latter reference the solvent extraction of the intermediate stage in the condensation is carried out under conditions which result in the intermediate products being retained in the aqueous layer containing the strong acid, which layer is then carried forward to the next stage without any reduction or elimination of the strong acid.

SUMMARY OF THE INVENTION

The invention comprises a process for the preparation of a mixture of di(aminophenyl)methane and oligomeric polymethylene polyphenyl polyamines which process comprises the steps of:

reacting aniline and formaldehyde, in a proportion of about 1.6 to about 8 moles of aniline per mole of formaldehyde, in the presence of an acid catalyst at a temperature in the range of about 0° C. to about 55° C. until the formation of aminobenzylamines is substantially complete;

adjusting, if necessary, the proportions of aniline and water in the resulting reaction mixture so that the molar proportion of aniline to formaldehyde originally present in the reaction mixture is at least 4:1, and the amount of water is such that the concentration of acid catalyst is in the range of about 1 to about 8 percent by weight;

subjecting the resulting aqueous solution to extraction with an inert organic solvent;

separating the solvent and aqueous layers;

removing the solvent and optionally part of the excess aniline from said solvent extract by distillation under reduced pressure;

subjecting the residual mixture of amines to rearrangement to the corresponding mixture of di(aminophenyl)methane and oligomeric polymethylene polyphenyl polyamines by heating at a temperature in the range of about 60° C. to about 115° C. in the presence of a catalyst selected from the class consisting of strong acids, diatomaceous earth, clay and zeolite, provided that, when a strong acid is employed as catalyst, it is present in an amount substantially less than that employed in the initial condensation of aniline and formaldehyde.

DETAILED DESCRIPTION OF THE INVENTION

The reaction between aniline and formaldehyde in the presence of a mineral acid such as hydrochloric acid has been the subject of considerable study over a prolonged period. It is generally recognized that the reaction occurs in two distinct stages—the second of which is generally conducted at relatively higher temperatures than the first. The various stages in the reaction so far as it relates to the preparation of the major product, namely di(aminophenyl)methane, can be represented schematically as follows:

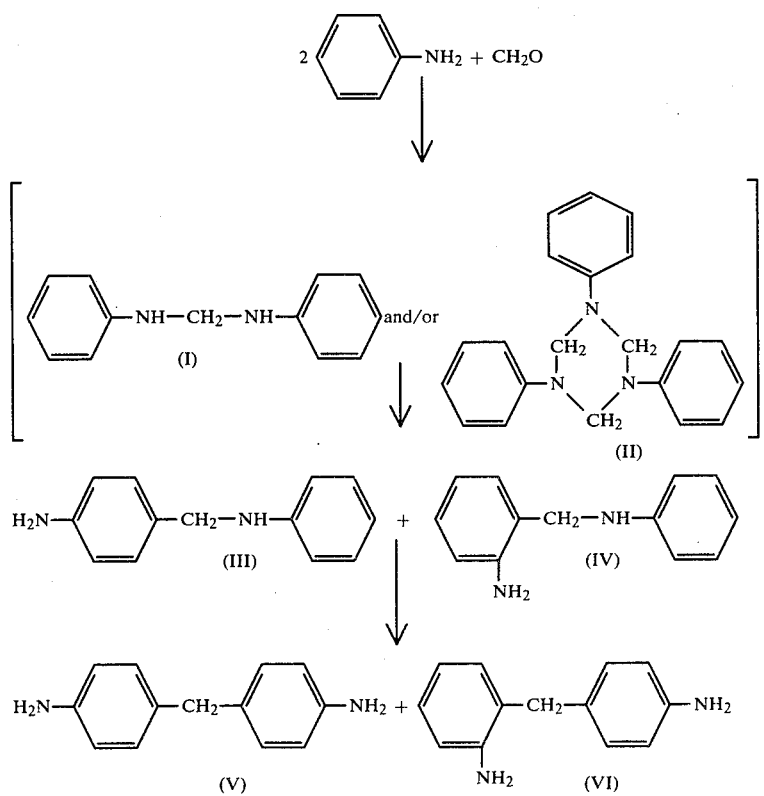

In the above condensation the aniline and formaldehyde react to form, as a highly transient intermediate, methylene dianiline (I). It is believed that the symmetrical N,N',N"-triphenylhexahydrotriazine (II) is also formed at this stage and that its subsequent behavior parallels the behavior of (I). The transient intermediates (I) and (II) then rearrange to form N-phenylaminobenzylamines. At least two such monomeric products are possible, namely, the p-isomer represented by the formula (III) and the corresponding o-isomer represented by the formula (IV). The principal isomer formed is normally the p-isomer (III) with the o-isomer as the minor component. As will be readily appreciated by one skilled in the art, the formation of the monomeric products (III) and (IV) is accompanied by formation of corresponding oligomeric products which can be represented by the generic formula

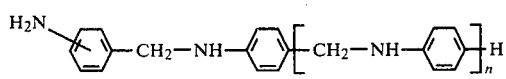

wherein the free amino group is o- or p- with respect to the —CH$_2$—NH— bridging group, the multiple —CH$_2$—NH— groups are o- or p- with respect to their immediate neighbors and n is a whole number. The mixture of isomers (III) and (IV), and the oligomeric forms thereof, is hereinafter referred to as the "aminobenzylamines".

In the final sequence of the above reaction, the aminobenzylamines (III) and (IV) rearrange to form the corresponding di(aminophenyl)methanes including the p,p'-isomer (V) and the o,p'-isomer (VI). It will be seen that rearrangement of the aminobenzylamines (III) and (IV) can also give rise to the o,o'-isomer of di(aminophenyl)methane although, in the interests of simplicity, this particular isomer is not shown in the reaction scheme since it is generally not formed in any substantial amounts. It will be appreciated by one skilled in the art that the oligomeric forms of the aminobenzylamines (III) and (IV), discussed above, will rearrange to give corresponding polymethylene polyphenyl polyamines but the formation of such products has not been shown in the above reaction scheme in the interests of simplicity.

Of the various stages shown in the above reaction, the first two, namely the formation of the transient intermediates (I) and (II) and their rearrangement to the corresponding aminobenzylamines (III) and (IV), generally occur when the aniline and formaldehyde are brought together in the presence of mineral acid at ambient temperatures, i.e., of the order of about 25° C. without the application of external heat. The reaction is exothermic and, unless controlled by cooling, the temperature of the reaction mixture will rise substantially.

The final stage of the above process, i.e., the rearrangement of the aminobenzylamines, will not take place to any significant degree until the reaction mixture is heated, generally to a temperature in excess of about 60° C.

In accordance with the process of the present invention the formation of the intermediate aminobenzylamines is carried out in accordance with any of the procedures hitherto employed in the art to achieve this first stage in the presence of a strong acid catalyst such as hydrochloric, hydrobromic, phosphoric, p-toluenesulfonic, methanesulfonic acids, and the like. A particularly preferred strong acid catalyst is hydrochloric acid. Advantageously, the aniline and formaldehyde are brought together under aqueous conditions in the presence of the strong acid and using appropriate agitation means. The order in which the reactants are brought together is not critical.

The reaction between aniline and formaldehyde is exothermic but can be controlled satisfactorily either by appropriate adjustment of the rate of addition of reactant or by applying external cooling or by a combination of both techniques. Although the reaction temperature in this stage of the reaction is not critical, it should not be lower than about 0° C. and it is preferable that the temperature in question does not rise above about 55° C. Preferably the reaction temperature at this stage of the reaction is maintained within the range of about 15° C. to 35° C.

The reaction between the aniline and formaldehyde to yield the intermediate aminobenzylamines in this first stage of the process of the invention occurs very rapidly. The progress of the reaction can be followed by conventional analytical techniques, e.g. by following the disappearance of formaldehyde from the reaction mixture. When the reaction is observed to have proceeded to completion, which is adjudged to be represented by formation of approximately 90 percent by weight of the expected aminobenzylamines, the next stage of the process of the invention is initiated as described below.

The proportions in which the aniline, formaldehyde and acid catalyst are brought together in the above first stage of the process of the invention are determinative of the overall yield of diamine in the final polyamine mixture and, to a certain extent, of the proportion of o,p'-isomer to p,p'-isomer in the diamine component of said final mixture. Advantageously, the proportion of aniline to formaldehyde is at least 1.6 moles of the former for each mole of the latter. While the lower limit of aniline concentration is critical in terms of the overall result achieved in the process, the upper limit is free from such criticality and is dictated largely by economic considerations. An upper limit of about 8 moles of aniline per mole of formaldehyde conforms to the latter considerations. Generally, the proportion of aniline employed in the first stage of the process of the invention is within the range of about 2 to about 2.8 moles per mole of formaldehyde but proportions higher or lower than this can be employed if desired.

The amount of strong acid catalyst employed in the first stage of the process of the invention is advantageously in the range of about 0.5 moles to about 1 moles per mole of aniline and is preferably within the range of about 0.7 moles to about 0.8 moles per mole of aniline.

In the second stage of the process of the invention the reaction product from the first stage, which product is an aqueous solution containing mainly the intermediate aminobenzylamines, excess aniline and hydrochloric acid, is then treated by the addition of the appropriate amounts of aniline (if any) and of water (if any) which are necessary to bring the overall molar ratio of aniline to the amount of formaldehyde originally present in the initial reaction mixture to a minimum of 4:1 and the overall concentration of hydrochloric acid to a value within the range of about 1 to about 8 percent by weight based on the total weight of the reaction mixture. Depending upon the proportion of aniline employed in the first stage of the reaction, it may or may not be necessary to add further aniline at this stage to achieve the above result. It is found that the above proportions of aniline and hydrochloric acid are necessary to ensure that the major part of the aminobenzylamines is extracted from the aqueous layer in the next step of the process.

Said next step comprises the extraction of the reaction product, after adjustment of aniline and hydrochloric acid concentrations have been made, using an inert organic solvent. By inert organic solvent is meant an organic solvent which does not enter into reaction with any of the components of the reaction product or interfere in any way with the desired end result of the process of the invention. Illustrative of inert organic solvents are benzene, toluene, xylene, monochlorobenzene, dichlorobenzene, and the like. A preferred inert organic solvent for use in the process of the invention is benzene.

The proportion in which the inert organic solvent is used in carrying out the extraction in accordance with this stage of the process of the invention can vary within wide limits but is advantageously in the range of about 1 parts by volume to about 5 parts by volume per each part by volume of the aqueous reaction mixture which is being extracted. Preferably, the amount of solvent employed is within the range of about 2.5 parts to about 3.5 parts by volume for each part by volume of the aqueous reaction mixture. The actual extraction can be carried out using any of the means commonly employed in the art for carrying out such extractions. For example, any of the known tube extractors and liquid extractors, mixers and phase separators conventionally employed in chemical processing may be used.

Contrary to the findings reported in the aforesaid British Specification No. 1,536,008, the solvent extraction of the above reaction mixture results in the transfer to the solvent phase of the major part of the aminobenzylamines together with part of the excess aniline originally present in the aqueous reaction mixture. The aqueous phase, which remains after the solvent extraction has been completed, contains a major part of the excess aniline and only a very minor proportion of the aminobenzylamines originally present in the reaction mixture, both the aniline and the aminobenzylamines being present as their salts with the strong acid catalyst used in the initial condensation.

The aqueous phase and the solvent phase are then separated and subjected to different treatment. The aqueous phase, after partial removal of water, if desired, is employed as part of the reactants required in a subsequent run of the process of the invention. Thus, this aqueous phase still contains the total acid catalyst employed in the initial condensation and can therefore supply the catalyst needed for the subsequent run. It is therefore only necessary to adjust the concentration of aniline in this aqueous phase to the desired level before bringing this recovered phase into contact with formaldehyde thus initiating the first step of a new run of the process of the invention.

The solvent phase from the above extraction step, optionally after washing with further amounts of water (any such water washings are combined with the aqueous phase remaining after the separation of the solvent extract), is then subjected to distillation under reduced pressure to remove the inert organic solvent and, if desired, part or all of the excess aniline present in the extract. When the distillation is employed to remove solvent only and not part of the aniline, the temperature employed will be relatively low and generally not higher than about 60° C. When it is required to remove part of the aniline as well as the solvent, it will be necessary to employ a higher temperature, after all solvent has been removed, in order to distill out the aniline. Temperatures up to about 150° C., depending upon the amount of vacuum employed, have been used.

Advantageously, the residue remaining after the distillation still contains of the order of 0.8 to 1.5 moles of aniline per mole of aminobenzylamines. This residue is then subjected to the final step of the process of the invention in which it is subjected to heating at a temperature of about 60° C. to about 115° C. in the presence of a catalyst until all the aminobenzylamines have been converted to methylene-bridged polyphenyl polyamines. This latter end point can be detected readily by removing aliquots of the reaction mixture from time to time and submitting the same to analysis by techniques such as infrared spectroscopy, gas liquid phase chromatography, high pressure liquid chromatography, nuclear magnetic resonance spectroscopy and the like.

The catalyst which is employed in this final stage of the process of the invention can be any of the strong acid catalysts employed as catalyst in the first stage of the process of the invention. However, it is found that the proportion of such catalysts which it is necessary to employ in this last step of the process of the invention is very substantially less than that which it was necessary to employ in the said first step. Thus, the proportion of strong acid catalyst employed in this final step of the process of the invention is only of the order of about 0.2 mole to about 0.9 mole per mole of aminobenzylamine and is preferably of the order of about 0.3 mole to about 0.7 mole per mole of aminobenzylamine.

Alternatively, rather than use a strong acid as catalyst in this final step, it is possible to employ a solid catalyst such as diatomaceous earth, a zeolite and or a clay. Such catalysts are described in great detail and exemplified in U.S. Pat. No. 4,039,581, Column 4, line 65 through Column 5, line 65 and this disclosure is incorporated herein by reference. When the reaction is carried out using a batch procedure, the amount of solid catalyst so employed is advantageously within the range of 5 to 30 percent by weight based on aminobenzylamines and aniline and is preferably within the range of 15 to 25 percent by weight based on aminobenzylamines. As will be obvious to one skilled in the art, the reaction can also be carried out on a continuous basis, the mixture of aminobenzylamines and aniline being passed through a bed or column of the solid catalyst.

When the above final stage of the process of the invention is judged to be complete, as determined by any of the analytical techniques discussed above, the reaction product is worked up using conventional procedures. Where a solid catalyst is employed in this step using a batch type procedure the catalyst is removed by centrifugation, filtration, and like procedures and the excess aniline, if any, is removed by distillation. Where a strong acid catalyst is used in the final step, the reaction mixture is neutralized using aqueous base such as sodium hydroxide and then washed with water before removing the excess aniline, if any, by distillation.

The mixture of diamines and higher oligomers so obtained generally contains from about 35 to about 90 percent of diaminodiphenylmethane, depending upon the proportions of aniline to formaldehyde used in the initial condensation. The proportion of 4,4'-isomer in the diamine present in the reaction mixture is generally at least about 92 percent by weight when strong acid catalyst is used, again depending upon the proportions of reactants employed in the initial condensation. When solid catalyst is used in the final step, the 4,4'-isomer is somewhat lower.

The mixture of methylene-bridged polyphenyl polyamines so obtained can be used in any one of a number of ways. For example, the mixture can be subjected to procedures such as fractional crystallization and fractional distillation under reduced pressure to separate the diamine content from the higher oligomers. The isolated diamine can be purified, if desired, using fractional crystallization or like techniques to obtain a product which is substantially pure 4,4'-isomer. The isolate diamine, after purification if desired, can then be used as such as a curative for epoxy resins or as an intermediate in the formation, by catalytic hydrogenation, of di(aminocyclohexyl)methane, which latter is itself useful as an intermediate, using methods well-known in the art, in the formation of polyamides, polyimides, and copolymers thereof. The isolated diamine can also be phosgenated to form the corresponding diisocyanate which finds wide application in the preparation of polyurethane and like polymers.

The oligomeric polyamines which remain after separation of the diamine in the above manner are also useful as curatives for epoxy resins and as intermediates in the preparation, by phosgenation, of the corresponding polymethylene polyphenyl polyisocyanates. The latter are widely known and used in the preparation of rigid polyurethane and polyisocyanurate foams and as adhesives and the like.

Alternatively, the mixture of diamine and oligomeric polyamines obtained in the process of the invention can be subjected, without separation of the individual components, to phosgenation to produce the corresponding mixture of methylenebis(phenyl isocyanates) and oligomeric polymethylene polyphenyl polyisocyanates. This mixture of isocyanates can be employed as such in the preparation of polyurethanes, polyisocyanurates and the like cellular and non-cellular polymers. On the other hand, the mixture of isocyanates can be separated into methylenebis(phenyl isocyanate) and a residue of the oligomeric polymethylene polyphenyl polyisocyanates using procedures such as those described in U.S. Pat. Nos. 3,471,543 and 3,892,634.

In order to facilitate further an understanding of the various steps of the process of the invention, reference is made to FIG. 1 which shows a schematic representation of said steps. The initial reactants, aniline, formaldehyde and strong acid catalyst, are brought together in the first stage reactor (2) and reacted under the conditions discussed above to produce a mixture of aminobenzylamines and unreacted aniline. This reaction product is admixed with additional aniline (if necessary) and water to bring the proportion of aniline to the minimum discussed above and to adjust the concentration of strong acid to the level discussed above. The resulting mixture is extracted with inert organic solvent (as above defined) in extractor (4). The solvent extract and the aqueous layer remaining after the extraction are separately removed from the extractor and subjected to different treatment. The solvent extract is, optionally, subjected to water washing in mixer-extractor (6) and the wash water, if any, is recovered and combined with the aqueous layer derived from extractor (4). The washed solvent extract is transferred to stripper (8) where the inert organic solvent is removed under reduced pressure, at temperatures discussed above, together with some of the excess aniline if desired. The recovered solvent and aniline can be returned to storage and or reused in a subsequent run of the process of the invention.

The residual mixture of amines recovered as bottoms from the stripper (8) is then transferred to the second stage reactor (10) wherein the mixture is converted to the desired end product in the presence of catalyst as discussed above. Where the catalyst employed in this stage of the reaction is a strong acid the reaction mixture from reactor (10) is subjected to neutralization in zone (12). Where the catalyst employed in the second stage reactor (10) is a solid this catalyst is removed by centrifugation, filtration or like techniques in zone (12). In the final step of the process the product remaining after neutralization or separation of the catalyst in zone (12) is subjected to distillation under reduced pressure in stripper (14) to remove excess aniline, which is returned to storage for reuse, and leave the desired polymethylene polyphenyl polyamine as the undistilled residue.

The aqueous phase recovered from extractor (4), comprises an aqueous solution of the salt of aniline with whatever strong acid was used in the initial condensation, together with a minor amount of aminobenzylamines also in the form of a salt with said strong acid. This aqueous phase, combined with any water washings from (6), can be concentrated, if desired, by partial removal of water therefrom in stripper (16), before being returned to the first stage reactor (2) for use in a subsequent run of the process of the invention. The recycling of this aqueous phase to the reactor (2) means that significantly reduced amounts of fresh aniline and substantially no additional acid catalyst need to be introduced into reactor (2) for the next run of the process.

As will be apparent from the description given above and the examples given below, the process of the invention has at least two significant advantages over processes hitherto employed in the art. Thus, the reaction mixture in the second stage reactor (10), which is operated at elevated temperatures, can be free of corrosive acid (when a solid catalyst is employed) or contains a markedly reduced amount of corrosive acid compared with previously employed processes. Further, the amount of acid which requires neutralization at the end of the reaction is either eliminated entirely or is markedly reduced as compared with previously employed processes. This represents a substantial reduction of, and possibly total elimination of, the necessity to dispose of large quantities of by-product salts generated by the neutralization. Other advantages, such as the ability to recover and reuse all the strong acid employed in the first condensation step, will be readily apparent to those skilled in the art.

The following examples describe the manner and process of making and using the invention and set forth the best mode contemplated by the inventors of carrying out the invention but are not to be construed as limiting.

EXAMPLE 1

A series of five consecutive runs were made in accordance with the process of the invention as follows.

In the first run a solution of 54.7 parts by weight (0.588 moles) of aniline in a solution of 53.47 parts by weight (0.471 mole) of 33 percent w/w hydrochloric acid was maintained at 30° C. with vigorous stirring while a total of 17.35 parts by weight (0.214 mole) of 37 percent w/w aqueous formaldehyde solution was added over a period of six (6) minutes. When the addition was complete, the mixture was stirred and maintained at 30° C. for a further five minutes. Thereafter a total of 104.5 parts by weight (1.124 moles) of additional aniline and 147.2 parts by weight (8.18 moles) of water was added to the reaction mixture with stirring and the mixture so obtained was subjected to extraction, manually using a separatory funnel, with three successive quantities (560, 280 and 280 parts by weight, respectively) of benzene. The benzene extracts were combined and washed with three portions of water each of 300 parts by weight. The water washings were combined with the aqueous phase remaining after the benzene extraction and the benzene solution and the aqueous phase (+washings) were then treated separately as follows:

(a) The benzene solution was subjected to distillation at 55° C. and a pressure of 100 mm. of mercury to remove benzene. Thereafter the pressure was lowered to 2 mm and the temperature increased to 77° C. to remove aniline and reduce the aniline content of the residue (weight 41.1 g.) to 37.7 percent by weight, the bulk of the remainder of the residue being aminobenzylamines. The residue was then admixed with 8 parts by weight of 33 percent hydrochloric acid and subjected to heating at 60° C. for 1 hour followed by 1 hour at 80° C. and a final hour at 100° C. The resulting product was cooled to room temperature, neutralized by the addition of 50 percent aqueous sodium hydroxide solution and the amine layer was separated. This amine product was shown by gel permeation chromatography to contain 19.5 percent by weight of aniline, the remainder of the mixture being methylene-bridged polyphenyl polyamines containing 79.2 percent by weight of di(aminophenyl)methane. The latter diamine was shown by gas liquid phase chromatography to contain 93.8 percent by weight of p,p'-isomer and 6.2 percent by weight of o,p'-isomer.

The aniline was separated from the above product by distillation under reduced pressure and recovered for use in a subsequent run.

(b) The aqueous layer remaining after the benzene extraction described above and the water washings of the benzene layer were combined and evaporated until a residue of 76.2 parts by weight remained. This residue was shown by a combination of analyses by gel permeation chromatography and nuclear magnetic resonance spectroscopy to contain 15.5 parts by weight of aniline, 11.7 parts by weight of hydrochoric acid, 42.3 parts by weight of water, 1.1 parts by weight of aminobenzylamines and 5.6 parts by weight of methylene-bridged polyphenyl polyamines.

This residue obtained in (b) was then reused as part of the reactants employed in a subsequent run, the amount of aniline being adjusted to the starting level (54.7 parts by weight) of the previous run and the amount of hydrochloric acid being adjusted to 17.2 parts by weight as in the previous run. The product resulting from these adjustments was then reacted with 37 percent aqueous formaldehyde as described for the above run and the whole procedure was carried through exactly as before. The recovered aqueous phase and washings from the benzene extraction were concentrated and reused in yet another run and the whole procedure was again repeated until a total of five runs had been carried out. The data from these runs is summarized in the following Tables. Table I summarizes the reaction conditions in the first condensation stage in each run together with the amounts and proportions of reactants including, in the case of runs 2–5, the amount of reactants derived from recycle of the aqueous phase from the previous run. Table II summarizes the conditions used in concentrating the aqueous phase together with the analysis of composition of the concentrate so obtained and that portion of the concentrate which was used in recycle. Table III gives details of the conditions used in the benzene and aniline stripping and analysis of the stripped product. Table IV gives the analysis of the rearranged final product and the methylene-bridged polyphenyl polyamines contained therein.

It is to be noted that, by reason of error in calculating the required quantity of aniline to be added to the aqueous phase recycle from Run 3 to prepare the starting reactants for Run 4 the amount of aniline used in Run 4 was significantly less than in the other runs and this resulted in the significant drop in diamine content of the product in Run 4 and the greatly reduced level of p,p'-isomer in this diamine.

TABLE I

Reaction conditions and reactants including recycle materials.

| Run Number | 1 | 2 | 3 | 4 | 5 |
|---|---|---|---|---|---|
| Formaldehyde: | | | | | |
| Addition Temp., °C. | 30 | 30 | 30 | 30 | 30 |
| Addition Time, min. | 6 | 12 | 9 | 5 | 7 |
| Hold Time, min. | 5 | 5 | 5 | 5 | 5 |
| Reactant Mole Ratios (including Reactant materials from Recycle): | | | | | |
| Aniline | 2.75 | 2.75 | 2.75 | 2.45* | 2.79 |
| Formaldehyde | 1 | 1 | 1 | 1 | 1 |
| Acid | 2.2 | 2.2 | 2.2 | 2.2 | 2.2 |
| Water | 12.25 | 15.53 | 15.63 | 12.33 | 12.25 |
| Fresh Raw Materials: pts. by wt. | | | | | |
| Aniline | 54.7 | 42.6 | 33.9 | 24.4* | 32.84 |
| Formaldehyde | 6.42 | 6.42 | 6.42 | 6.42 | 6.42 |
| Acid | 17.2 | 7.95 | 6.1 | 6.68 | 6.64 |
| Water | 47.2 | 26.53 | 38.3 | 27.37 | 26.58 |
| Recycle Raw Materials: pts. by wt. | | | | | |
| Aniline | 0 | 12.2 | 20.8 | 24.36 | 22.65 |
| Formaldehyde | 0 | 0 | 0 | 0 | 0 |
| Acid | 0 | 9.21 | 11.1 | 10.47 | 10.56 |
| Water | 0 | 33.31 | 21.9 | 20.13 | 20.62 |
| Benzylamines | 0 | 0.87 | 2.6 | 2.24 | 3.52 |
| PAPA | 0 | 4.41 | 3.57 | 2.8 | 2.63 |
| Materials added after first cond.: pts. by wt. | | | | | |
| Aniline | 104.5 | 104.5 | 104.5 | 104.5 | 104.5 |
| Water | 147.2 | 147.2 | 147.2 | 147.2 | 147.2 |
| Benzene: pts. by wt. | 1121.2 | 1187.1 | 1187.1 | 1187.1 | 1187.1 |

*Reduced amount of aniline due to error in calculation

TABLE II

Processing of aqueous layer from benzene extraction.

| Run Number | 1 | 2 | 3 | 4 | 5 |
|---|---|---|---|---|---|
| Amount before stripping: pts. by wt. | 1245.8 | 508.5 | 506.8 | 535.5 | 508.5 |
| Stripping Conditions: | | | | | |
| Pressure, mm. Hg. | 50 | 50 | 50 | 50 | 50 |
| Temperature, °C. | 80 | 80 | 80 | 80 | 80 |
| Composition of concentrate, pts. by wt. | | | | | |
| Aniline | 15.5 | 31.0 | 37.8 | 35.6 | 36.18 |
| Acid | 11.7 | 16.5 | 16.25 | 16.6 | 15.83 |
| Water | 42.3 | 32.6 | 31.23 | 32.44 | 34.66 |
| Aminobenzylamines | 1.1 | 3.9 | 3.47 | 6.26 | 3.49 |
| Polyphenylpolyamine | 5.6 | 5.3 | 4.35 | 4.65 | 6.93 |
| Concentrate used for Recycle, pts. by wt. | | | | | |
| Aniline | 12.2 | 20.8 | 24.36 | 21.86 | 22.36 |
| Acid | 9.21 | 11.1 | 10.47 | 10.56 | 9.78 |
| Water | 33.31 | 21.9 | 20.13 | 20.64 | 21.42 |
| Aminobenzylamines | 0.87 | 2.6 | 2.24 | 3.98 | 2.16 |
| Polyphenylpolyamines | 4.41 | 3.57 | 2.8 | 2.96 | 4.28 |

TABLE III

Stripping of benzene; rearrangement; analysis of product.

| Run Number | 1 | 2 | 3 | 4 | 5 |
|---|---|---|---|---|---|
| Extract Composition, pts. by wt. | | | | | |
| Benzene | 1121.2 | 1187.1 | 1187.1 | 1187.1 | |
| Aniline | 67.49 | 67.93 | 71.61 | 59.97 | not analyzed |
| BA | 38.28 | 32.77 | 28.59 | 28.93 | |
| Benzene Stripping: | | | | | |
| Pressure, mm. Hg. | 100 | 100 | 100 | 100 | 100 |
| Temperature, °C. | 55 | 60 | 50 | 45 | 46 |
| GPC Analysis of Stripped Extract: | | | | | |
| % Aniline + Benzene | 70.03 | 74.72 | 71.33 | 79.59 | 67.86 |
| % BA | 29.97 | 25.28 | 28.67 | 20.41 | 32.14 |
| Composition of Stripped Extract, pts. by wt. | | | | | |
| Aniline + Benzene | 75.49 | 106.25 | 94.2 | 102.6 | 98.19 |
| BA | 32.31 | 35.95 | 37.8 | 26.31 | 46.5 |
| Aniline Stripping: | | | | | |
| Pressure, mm. Hg. | 2.0 | 1.8 | ~20 | ~20 | ~20 |
| Temperature, °C. | 77 | 75 | 90 | 90 | 90 |
| Aniline Stripped Extract Comp. pts. by wt. | | | | | |
| Aniline | 15.74 | 8.79 | 9.18 | 5.2 | 7.48 |
| Aminobenzylamines | 24.05 | 33.11 | 34.82 | 26.6 | 30.46 |
| Di(aminophenyl)methane | 0.35 | — | — | — | 1.56 |
| Rearrangement* Reaction Starting Composition, wt. % | | | | | |
| % Aniline | 20 | 26.96 | 20.07 | 20.09 | 20.1 |
| % Benzylamines | 46.9 | 45.35 | 46.78 | 46.88 | 46.9 |
| % Acid | 4.3 | 4.18 | 4.31 | 4.32 | 4.3 |
| % Water | 28.9 | 23.51 | 28.84 | 28.70 | 28.7 |

*Rearrangement Conditions: 2 hrs. @ 60° C., 1 hr. @ 80° C., 1 hr. @ 100° C.

TABLE IV

Analysis of final product before aniline stripping.

| Run Number | 1 | 2 | 3 | 4 | 5 |
|---|---|---|---|---|---|
| % wt. of aniline | 19.5 | 15.77 | 17.37 | 16.37 | 13.01 |
| % wt. of polyamines | 80.5 | 84.23 | 82.63 | 83.63 | 86.99 |
| GPC[1] Analysis of polyamines | | | | | |
| Diamine % wt. | 79.2 | 74.12 | 75.9 | 43.92 | 73.53 |
| Trimer % wt. | 16.5 | 18.23 | 18.12 | 25.98 | 18.41 |
| Tetra % wt. | 3.7 | 5.33 | 4.62 | 12.63 | 8.06 |
| Pentamer % wt. | 0.6 | 2.31 | 1.37 | 8.33 | — |
| Hexamer % wt. | — | — | — | 9.14 | — |
| Isomer analysis in diamine (GLC[2]) | | | | | |
| p,p'-isomer % wt. | 93.8 | 91.59 | 93.47 | 82.27 | 94.2 |
| o,p'-isomer % wt. | 6.2 | 8.21 | 6.43 | 16.92 | 5.71 |
| o,o'-isomer % wt. | 0.1 | 0.20 | 0.10 | 0.81 | 0.09 |

[1]GPC = gel permeation chromatography
[2]GLC = gas liquid chromatography

EXAMPLE 2

Four separate runs were carried out in accordance with the process of the invention using the following procedure. In each run the aniline, in solution in the hydrochloric acid, was admixed with the aqueous formaldehyde (in the mole ratios of reactants shown in Table V below) in a continuous tubular reactor at a temperature of about 41° C. and under turbulent flow conditions and an aliquot (amount shown in Table V) of the resulting reaction mixture was taken from the reactor. The aliquot was, in each case, admixed with aniline and water in the amounts shown in Table V and then extracted with benzene again in the amounts shown in Table V. The benzene extracts were separated and washed twice with water before being distilled under reduced pressure (conditions given in Table V) to remove benzene. The residue was then admixed with attapulgus clay (A RVM: Engelhard: previously calcined for 3 hrs. at 500° C.) in the amounts shown in Table V and heated at the temperature(s) and for the times shown in said Table. At the end of the heating period the reaction product was separated from the clay catalyst by filtration. The filtrate was distilled under reduced pressure to remove excess aniline and leave a mixture of methylene-bridged polyphenyl polyamines having the composition shown in Table V.

The aqueous phase remaining after the extraction with benzene in each of the runs contained all of the hydrochloric acid present in the original reaction mixture together with aniline and could be utilized as part of the reaction mixture employed in a subsequent run in accordance with the invention.

TABLE V

| Run Number | 6 | 7 | 8 | 9 |
|---|---|---|---|---|
| Benzylamines Production | | | | |
| Moles Aniline | 3 | 2.8 | 3 | 3.8 |
| Moles Formaldehyde | 1 | 1 | 1 | 1 |
| Moles Acid | 2.4 | 2.1 | 2.1 | 1.3 |
| Moles Water | 12.7 | 11.5 | 11.5 | 8.2 |
| Extraction | | | | |
| Condensation Rxn. Prod., gms. | 235 | 245 | 245 | 245 |
| Added Aniline, gms. | 98.6 | 114.4 | 105.7 | 161.3 |
| Added Water, gms. | 607.1 | 95.9 | 101.9 | 76.9 |
| Added Benzene, gms. | 823.6 | 1400 | 1050 | 724.8, 362.4, 362.4* |
| Benzene Stripping | | | | |
| Pressure, mm. Hg. | 3-645 | 49-92 | 61 | 11.5 |
| Temperature, °C. | 5-140** | 18-44 | 23-35 | 22-40 |

TABLE V-continued

| Run Number | 6 | 7 | 8 | 9 |
|---|---|---|---|---|
| Composition after benzene Stripping | | | | |
| % by wt. Benzylamines | 35 | 35 | 35 | 30 |
| % by wt. Aniline | 65 | 65 | 65 | 70 |
| Rearrangement Rxn. | | | | |
| % by wt. Benzylamines + Aniline | 80 | 90 | 80 | 83 |
| % by wt. Catalyst | 20 | 10 | 20 | 17 |
| gms. Aniline | — | — | — | 40.3 |
| gms. Benzylamines + Aniline | 194 | 341.6 | 122.4 | 213 |
| gms. Catalyst | 49 | 32.9 | 30.6 | 50.8 |
| Rearrangement Rxn. Conditions | 107° C., 21 hrs. | 95° C., 5 hrs. | 60° C., 3 hrs. 90° C., 2 hrs. 130° C., 1 hr. | 95° C., 16 hrs. |
| Product Analysis | | | | |
| Gel permeation chromatography | | | | |
| % di(aminophenyl)methane | 82.6 | 90.9 | 80.8 | 71.3 |
| % Trimer | 14.4 | 8.9 | 15.2 | 19.1 |
| % Tetramer | 3.0 | 0.2 | 4.0 | 9.6 |
| Composition of diamine in product (gas liquid chromatography) | | | | |
| % 4,4'-isomer | 86.5 | 85.8 | 85.1 | 90.1 |
| % 2,4'-isomer | 12.1 | 13.1 | 13.5 | 8.6 |
| % 2,2'-isomer | 1.4 | 1.1 | 1.4 | 1.3 |

*Extraction carried out in three stages.
**High temperature used to remove aniline.

We claim:
1. In a process for the preparation of a mixture of di(aminophenyl)methane and oligomeric polymethylene polyphenyl polyamines the steps comprising:
   reacting aniline and formaldehyde in a proportion of about 1.6 moles to about 8 moles of aniline per mole of formaldehyde in the presence of an acid catalyst at a temperature in the range of about 0° C. to about 55° C. until the formation of aminobenzylamines is substantially complete;
   adjusting, if necessary, the proportions of aniline and water in the resulting reaction mixture so that the molar proportion of aniline to formaldehyde originally present in the reaction mixture is at least 4:1 and the amount of water is such that the concentration of acid catalyst is in the range of about 1 to about 8 percent by weight based on the total weight of the reaction mixture;
   subjecting the resulting aqueous solution to extraction with an inert organic solvent;
   separating the solvent and aqueous layers;
   removing the solvent from said solvent extract by distillation under reduced pressure;
   subjecting the residual mixture of amines to rearrangement to the corresponding mixture of di(aminophenyl)methane and oligomeric polymethylene polyphenyl polyamines by heating at a temperature in the range of about 60° C. to about 115° C. in the presence of a catalyst selected from the class consisting of strong acids, diatomaceous earth, clay and zeolite, provided that, when a strong acid is employed as catalyst, it is present in an amount substantially less than that employed in the initial condensation of the aniline and formaldehyde.

2. The process of claim 1 wherein the aqueous phase, remaining after the solvent extraction, is recovered and incorporated into the reaction mixture employed in a subsequent condensation of aniline and formaldehyde.

3. The process of claim 1 wherein the acid catalyst employed in the initial condensation and in the rearrangement step is hydrochloric acid.

4. The process of claim 1 wherein the organic solvent employed in the extraction step is benzene.

5. The process of claim 1 wherein the catalyst employed in the rearrangement step is diatomaceous earth.

6. The process of claim 1 wherein the catalyst employed in the rearrangement step is attapulgus clay.

7. The process of claim 1 wherein the catalyst employed in the rearrangement step is zeolite.

8. The process of claim 1 wherein a portion of the excess aniline is removed during the distillation step utilized to remove solvent.

* * * * *